United States Patent [19]

Dahan

[11] 4,375,355

[45] Mar. 1, 1983

[54] ORTHOPAEDIC DENTOFACIAL CORRECTION APPLIANCE

[75] Inventor: Jose Dahan, Kraainem, Belgium

[73] Assignee: Dentaurum H.P. Winkelstroeter KG, Ispringen, Fed. Rep. of Germany

[21] Appl. No.: 112,286

[22] Filed: Jan. 15, 1980

[30] Foreign Application Priority Data

Jan. 17, 1979 [BE] Belgium .................................. 873533

[51] Int. Cl.³ .............................................. A61C 7/00
[52] U.S. Cl. ...................................................... 433/5
[58] Field of Search ........................................ 433/5, 6

[56] References Cited

U.S. PATENT DOCUMENTS

| | | | |
|---|---|---|---|
| 2,334,894 | 11/1943 | Atkinson | 433/5 |
| 3,401,457 | 9/1968 | Hickham | 433/8 |
| 3,514,860 | 6/1970 | Stifter | 433/5 |
| 4,115,921 | 9/1978 | Armstrong | 433/5 |
| 4,167,061 | 9/1979 | Forster | 433/5 |

*Primary Examiner*—Robert Peshock
*Attorney, Agent, or Firm*—Shenier & O'Connor

[57] ABSTRACT

An orthopaedic appliance for correcting deformities of the lower jaw wherein gross forces on the mandible joints from forces applied to the chin are appreciably reduced by applying opposing forces in the region of the molars.

9 Claims, 2 Drawing Figures

ORTHOPAEDIC DENTOFACIAL CORRECTION APPLIANCE

The invention relates to an orthopaedic dentofacial appliance for correction of shape and position deformities of the mandible and also to a method of using such a correction appliance.

Orthopaedic dentofacial correction appliances of the aforementioned kind serving the special purpose of treating shape and position deformities of the mandible are already known, more particularly, in the form of chin-engaging fixtures and the like, and also mask-like correction appliances (vide German Utility Model No. 7 122 998), also referred to as Delaire masks. A chin-engaging fixture enables a rearwardly directed force to be applied to the patient's chin, while a forwardly directed force can be applied with the mask-like appliances supported at the forehead and chin. In particular, the mask-like appliances exploit a force of reaction occurring on account of a forwardly directed pulling force exerted on the maxilla to act with this force of reaction on the mandible. In the case of both known appliances, the mandible moves from its initial position on account of the force applied to the patient's chin and the ends of the mandible joints come to rest against the joints in the temple area of the skull so that a force of reaction of substantially the same size, but in the opposite direction of that exerted on the patient's chin is applied to the mandible joints. The force applied to the chin and the force effective in the area of the joints form a couple in such a direction that an increase in the opening angle of the mandible or a rearward rotation of the front portion of the mandible and an enlargement of the lower half of the face are obtained.

These effects on the growth and shape of the lower jaw limit employment of the currently known correction appliances to treatment of protruding mandibles with forward or clockwise rotation. Moreover, the strain on the joints results in undesired side-effects, for example, pains in or damage to the joints, which frequently persist even after termination of the treatment and are due to the relatively strong forces applied at the mandible joints.

Based on the prior art, the object underlying the invention is to provide a correction appliance of the first aforementioned kind which is also suitable for treatment of a protruding lower jaw with rearward rotation and is so constructed that only very slight forces, if any at all, occur in the mandible joint area.

This object is attained with an orthopaedic dentofacial correction appliance according to the invention in that first means are provided for applying a force in the area of molars on the right and left side of the lower jaw and second means for exerting a force on the chin.

The decisive advantages of the correction appliance according to the invention are due to the fact that the anchorage occurs in the area of the molars of the lower jaw (genio-molar anchorage).

A particularly preferred embodiment of an appliance according to the invention is characterized in that the first means comprise a face bow having two legs pointing while in use in the direction of the back of the patient's head and connected to each other substantially in front of the patient's mouth, in that the free ends of the two legs of the face bow are connected to a device resting against the patient's head to apply a pulling force to each of the legs, in that two arms extending while in use into the patient's mouth and supported at fixtures on the molars are connected to the face bow, and in that the second means comprise a chin cup fastened to the face bow.

A further advantageous embodiment of the invention is characterized in that the chin cup is fastened to the face bow by substantially rigid members, in that the chin cup comprises a rigid cup lined on the inside with an elastic material and shaped so as to conform with the shape of the patient's chin, and in that the rigid fastening members for the chin cup consist of two rigid brackets both secured at one end to the rigid cup and at the other end to the face bow.

Further details and advantages of the invention are explained at greater length in the following with reference to the drawings and/or constitute the subject matter of subclaims.

In both Figures the main parts of the patient's head are shown in the position assumed while the appliance is in use.

Figure 1:
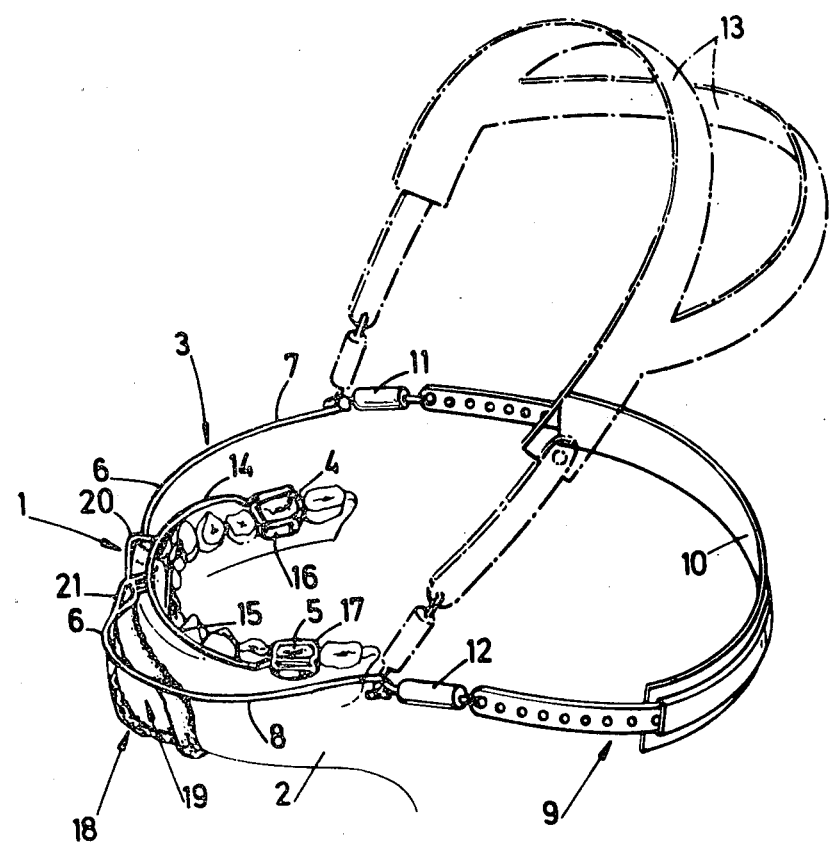
FIG. 1 is a perspective illustration of a preferred embodiment of an orthopaedic correction appliance in accordance with the invention.

FIG. 1 illustrates in thick unbroken lines a preferred embodiment of an orthopaedic dentofacial correction appliance according to the invention for treatment of a protruding mandible with rearward rotation, while the thinner unbroken lines illustrate part of the mandible or lower jaw 2 of a patient wearing the correction appliance.

The correction appliance includes first means 3 for the purpose of exerting a force on a right molar 4 and the associated molar 5 of the mandible 2. The first means 3 comprise a face bow 6 having two legs 7, 8 facing the back of the patient's head while the appliance is in use. The legs 7 and 8 are connected to each other substantially in front of the patient's mouth while their free ends are in the form of hooks connected to a device 9 enabling pulling forces of equal strength and directed towards the back of the patient's head to be exerted on the two legs 7, 8 of the face bow. The device 9 illustrated in unbroken lines in FIG. 1 is specially designed for treatment of a protruding mandible with rearward rotation and comprises a neck strap 10 of adjustable length supported at the nape of the patient's neck when the correction appliance is in use, with its free ends connected to the free ends of the legs 7, 8 by dynamometers 10 and 12 in the form of spring balances enabling measurement of the forces exerted on the legs 7, 8. These pulling forces can be regulated by adjustment of the length of the strap 10.

In a variant of the above-described embodiment illustrated in FIG. 1, specially designed for treatment of a protruding mandible with forward rotation, the device for exerting pulling forces on the legs 7 and 8 includes a headband 13 of adjustable length supported at the crown of the patient's head when the correction appliance is in use, with its ends connected to the free ends of the legs 7 and 8. For certain special applications, the headband 13 may be employed simultaneously with the neck strap device 9.

Fastened to the face bow 6 in the area located in front of the patient's mouth when the appliance is in use are two arms 14 and 15 extending into the patient's mouth, preferably in alignment with the outer contour of the row of teeth and each entering a sleeve or small tube provided on an orthodontic fixture 16, 17 on the right and left molars 4, 5, respectively. Each of the arms 14, 15 or the associated sleeve comprises a stop means to retain the fixtures 16, 17 and the arms 14, 15 in a predetermined mutual position while the appliance is in use.

The correction appliance 1 furthermore comprises means 18 for exerting a force on the patient's chin. These means 18 include a chin cup 19 connected to the face bow 6 by two substantially rigid rods or brackets 20 and 21. The chin cup 19 itself consists of a cap 22 made of synthetic material which fits onto the patient's chin snugly and is lined on the inside with a synthetic foam material so as to rest softly against the patient's chin. The first ends of the brackets 20, 21 are embedded in the chin cup 19, while their other ends are soldered or welded to the face bow 6.

Figure 2:
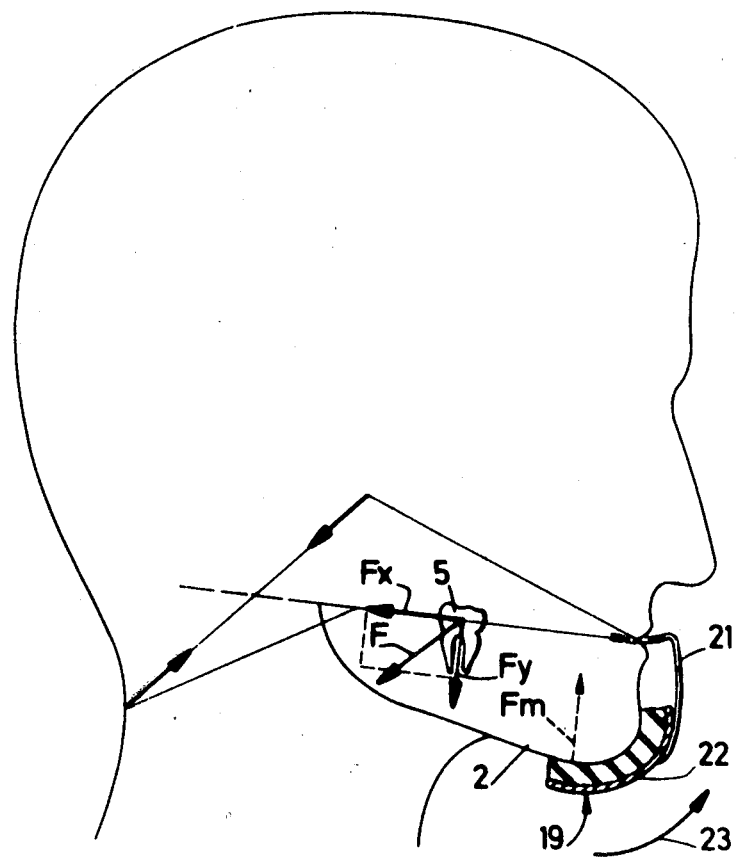
FIG. 2 is a schematic illustration to explain the forces exerted on the patient's mandible by the correction appliance according to the invention.

FIG. 2 is a schematic illustration to explain the effect of the correction appliance for treatment of a protruding mandible with rearward rotation, drawn in thick unbroken lines in FIG. 1. In this case, the correction appliance is provided with a nape support corresponding to the device 9. To treat a protruding mandible with rearward rotation, the mandible must be subjected to a force in the direction of the arrow 23.

As is shown in FIG. 2, the correction appliance 1 according to the invention enables a force F to be exerted on the molars 4 and 5. This force F can be resolved into a horizontal component $F_x$ and a vertical component $F_y$. An opposed force of reaction $F_m$ exerted on the patient's mandible 2 by the chin cup 19 corresponds to the vertical component $F_y$ of the forces F. Furthermore, the horizontal component $F_x$ of the force F can be varied, i.e., reduced or slightly increased, in the course of the treatment. To this end, one can in the course of treatment of a protruding mandible with, for example, rearward rotation, raise or lengthen the legs 7 and 8 or lower the support at the nape of the neck, which enables the vertical component $F_y$ to be increased and the horizontal component $F_x$ to be reduced. If, on the other hand, the horizontal component $F_x$ is to be increased, the legs 7, 8 can be lowered or shortened or the nape support device 9 raised.

To treat a protruding mandible with forward rotation, a couple of forces must be allowed to act thereon in a direction opposite to that of the arrow 23, which is enabled by a crown support, for example, in the form of a headband 13. In this case, the vertical component $F_y$ is opposed to the vertical component illustrated in FIG. 2, and a force of reaction to this vertical component can be obtained by way of the chin cup 19 if the latter is pressed tightly against the patient's chin.

It is apparent from the above description that the invention is in no way limited to the embodiment referred to hereinabove. On the contrary, numerous modifications and/or additions can be made to the embodiment without departing from the basic concept underlying the invention.

I claim:

1. An orthopaedic dentofacial appliance for the correction of shape and position deformities of a lower mandible carrying a pair of molars on left and right rearwardly extending portions thereof and having a chin portion and a transverse axis characterized in the provision of first relatively rigid frame having first portions for engaging said molars to exert a first force on said mandible in the region of said molars and in a first direction and a second portion for exerting a second force on said chin portion in a direction at an angle to said first direction and means for applying a force to said frame at a location between said first portions and said second portion to cause said portions to exert said first and second forces to exert a couple on said mandible tending to rotate said mandible around said transverse axis in a direction to correct a deformity.

2. Appliance as defined in claim 1, characterized in that the means comprise a face bow having two legs pointing while in use in the direction of the back of the patient's head and connected to each other substantially in front of the patient's mouth, in that the free ends of the two legs of the face bow are connected to a device supported by the patient's head for exerting a pulling force on each of the legs, in said first frame portions comprise two arms extending while in use into the patient's mouth and supported at fixtures of the molars are connected to the face bow, and in that the second frame portion comprises a chin cup fastened to the face bow.

3. Appliance as defined in claim 2, characterized in that the chin cup is fastened to the face bow by substantially rigid members.

4. Appliance as defined in claim 3, characterized in that the chin cup comprises a rigid cup lined with an elastic material on the inside and shaped so as to conform with the shape of the patient's chin, and in that the rigid fastening members for the chin cup are two rigid brackets both secured at one end to the rigid cup and at the other end to the face bow.

5. Appliance as defined in claim 2, characterized in that each of the fixtures comprises a small tube which the free end of the respective arm enters, and in that the arms and/or the tubes comprise stop means to retain the aforementioned members in a predetermined mutual position while in use.

6. Appliance as defined in claim 2, characterized in that the device exerting a pulling force on the two legs of the face bow is so constructed that the pulling force is exerted in the direction of the back of the patient's head.

7. Appliance as defined in claim 2, characterized in that the device exerting a pulling force comprises a strap adjustable in length and supported at the nape of the patient's neck.

8. Appliance as defined in claim 2, characterized in that the device exerting a pulling force on the two legs of the face bow comprises a headband connected to the free ends of the legs of the face bow and supported while in use at the crown of the patient's head.

9. Appliance as defined in claim 2, characterized in that the device exerting the pulling force comprises at least one dynamometer enabling measurement of the pulling force exerted.

* * * * *